United States Patent
Feucht et al.

(12)
(10) Patent No.: US 6,395,684 B1
(45) Date of Patent: May 28, 2002

(54) SELECTIVE HERBICIDES BASED ON A SUBSTITUTED PHENYL SULFONYL AMINO CARBONYL TRIAZOLINONE

(75) Inventors: Dieter Feucht, Monheim (DE); Hans-Joachim Santel, Leawood, KS (US); Klaus Lürssen, Bergisch Gladbach (DE); Ingo Wetcholowsky, Vinhedo (BR); Peter Dahmen, Neuss; Klaus-Helmut Müller, Düsseldorf, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/806,251
(22) PCT Filed: Sep. 21, 1999
(86) PCT No.: PCT/EP99/06990
§ 371 (c)(1), (2), (4) Date: Apr. 27, 2001
(87) PCT Pub. No.: WO00/19826
PCT Pub. Date: Apr. 13, 2000

(30) Foreign Application Priority Data

Oct. 2, 1998 (DE) .......................... 198 45 408

(51) Int. Cl.$^7$ .......................... A01N 43/653
(52) U.S. Cl. .......................... 504/273
(58) Field of Search .......................... 504/273

(56) References Cited

U.S. PATENT DOCUMENTS 5,534,486 A 7/1996 Müller et al. ............... 504/273
5,652,372 A 7/1997 Müller et al. ............ 548/263.4

FOREIGN PATENT DOCUMENTS

| CA | 2027206 | 12/1997 |
| CA | 2064636 | 12/1997 |
| EP | 0 341 489 | 8/1995 |
| WO | 98/12923 | 4/1998 |

*Primary Examiner*—S. Mark Clardy
(74) *Attorney, Agent, or Firm*—Joseph C. Gil; John E. Mrozinski, Jr.

(57) ABSTRACT

The present invention relates to selective-herbicidal compositions, characterized in that they contain an effective amount of the compound 2-(2-methoxycarbonyl-phenylsulphonylaminocarbonyl)-4-methyl-5-propoxy-2,4-dihydro-3H-1,2,4-triazol-3-one of the formula (I)

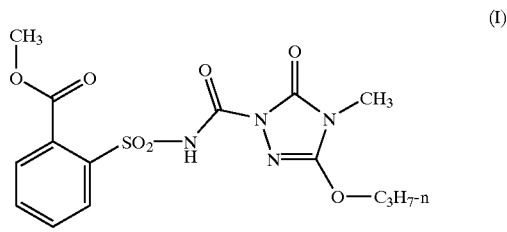

and/or of salts of the compound of the formula (I), and to the use of these compositions for the selective control of weeds in crops of cereals, in particular crops of wheat, and to methods for the selective control of weeds in crops of cereals by applying the compositions together with surfactants and/or customary extenders.

9 Claims, No Drawings

SELECTIVE HERBICIDES BASED ON A SUBSTITUTED PHENYL SULFONYL AMINO CARBONYL TRIAZOLINONE

FIELD OF THE INVENTION

The invention relates to the use of the known compound 2-(2-methoxycarbonyl-phenylsulphonylaminocarbonyl)-4-methyl-5-propoxy-2,4-dihydro-3H-1,2,4-triazol-3-one of the formula (I) shown below—alias methyl 2-[[[(4,5-dihydro-4-methyl-5-oxo-3-propoxy-1H-1,2,4-triazol-1-yl)-carbonyl]-amino]-sulphonyl]-benzoate (CAS-Reg.-No.: 145026-81-9)—and its salts, in particular its sodium salt (CAS-Reg.-No. 181274-15-7), for the selective control of weeds in crops of useful plants, in particular for controlling problematic weeds in cereals.

BACKGROUND OF THE INVENTION

Substituted phenylsulphonylaminocarbonyltriazolinones such as, for example, the compounds 2-(2-methoxycarbonyl-phenylsulphonylaminocarbonyl)-4-methyl-5-butoxy-2,4-dihydro-3H-1,2,4-triazol-3-one, 2-(2-methoxycarbonyl-phenylsulphonylaminocarbonyl)-4-methyl-5-ethoxy-2,4-dihydro-3H-1,2,4-triazol-3-one, 2-(2-methoxycarbonyl-phenylsulphonylaminocarbonyl)-4-methyl-5-isopropoxy-2,4-dihydro-3H-1,2,4-triazol-3-one, 2-(2-ethoxycarbonyl-phenylsulphonylaminocarbonyl)-4-methyl-5-propoxy-2,4-dihydro-3H-1,2,4-triazol-3-one, 2-(2-methoxycarbonyl-phenylsulphonylaminocarbonyl)-4-propoxy-5-methyl-2,4-dihydro-3H-1,2,4-triazol-3-one and 2-(2-methoxycarbonyl-phenylsulphonylaminocarbonyl)-4-ethyl-5-propoxy-2,4-dihydro-3H-1,2,4-triazol-3-one and their salts, processes for preparing these compounds and their use as herbicides are the subject of earlier patent applications (cf. EP-341 489, EP-422 469, EP-507 171, U.S. Pat. No. 5,534,486). The individual abovementioned substituted phenylsulphonylaminocarbonyltriazolinones have a molecular structure which is very similar to that of the compound (I) to be used according to the invention but, in contrast to this compound, they show shortcomings in their activity or activity gaps in the case of certain weeds.

SUMMARY OF THE INVENTION

Selective-herbicidal compositions comprise an effective amount of the compound 2-(2-methoxycarbonyl-phenylsulphonylaminocarbonyl)-4-methyl-5-propoxy-2,4-dihydro-3H-1,2,4-triazol-3-one.

DETAILED DESCRIPTION

Surprisingly, it has now been found that the compound 2-(2-methoxycarbonylphenylsulphonylaminocarbonyl)-4-methyl-5-propoxy-2,4-dihydro-3H-1,2,4-triazol-3-one (I) and salts thereof, in particular the sodium salt of the compound of the formula (I), in comparison with the abovementioned structurally similar compounds, show considerably stronger activity against some weeds in cereal crops which are difficult to control, combined with very good compatibility with cereal species, such as, in particular, wheat, and are therefore particularly suitable for the efficient and selective control of weeds in cereals, in particular in wheat. The activity gaps observed with the abovementioned comparative compounds which are closely related to (I) do not occur in the weed spectrum of the compound (I) and its salts.

The invention provides selective-herbicidal compositions, characterized in that they contain an effective amount of the compound 2-(2-methoxycarbonyl-phenylsulphonylaminocarbonyl)-4-methyl-5-propoxy-2,4-dihydro-3H-1,2,4-triazol-3-one of the formula (I)

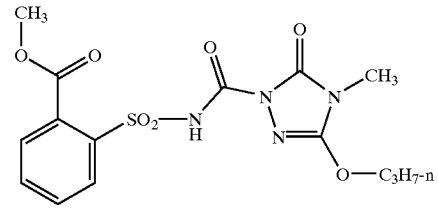

and/or of salts of the compound of the formula (I), in particular of their sodium salt [referred to as "(I)-Na-salt" in the use examples].

The invention furthermore provides the use of the compound 2-(2-methoxycarbonylphenylsulphonylaminocarbonyl)-4-methyl-5-propoxy-2,4-dihydro-3H-1,2,4-triazol-3-one of the formula (I) and/or of salts of the compound of the formula (I), in particular of its sodium salt, for the selective control of weeds in crops of cereals, in particular in crops of wheat.

The invention furthermore provides a method for the selective control of weeds in crops of cereals, in particular in crops of wheat, which is characterized in that the compound 2-(2-methoxycarbonyl-phenylsulphonylaminocarbonyl)-4-methyl-5-propoxy-2,4-dihydro-3H-1,2,4-triazol-3-one of the formula (I) and/or salts of the compound of the formula (I), in particular its sodium salt, is/are applied with surfactants and/or customary extenders in crops of cereals.

The compound of the formula (I) and its Na salt are already known (cf. U.S. Pat. No. 5,534,486—Examples 72 and 320).

The compound of the formula (I) and its salts have a broad herbicidal activity. They can be used, for example, for controlling the following weeds:

Dicotyledonous weeds of the orders: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura, Viola, Galeopsis, Papaver, Centaurea, Trifolium, Ranunculus, Taraxacum.

Monocotyledonous weeds of the orders: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Aegilops, Phalaris.

However, the use of the compound (I) and its salts is by no means limited to these orders but extends in the same manner to other plants as well.

The compound of the formula (I) and its salts have strong herbicidal activity and a broad spectrum of activity when used on the soil and on above-ground parts of plants. They are suitable for the selective control of monocotyledonous and dicotyledonous weeds in monocotyledonous crops, especially in cereals, in particular in wheat, both by the preemergence and by the post-emergence method.

Problematic weeds which can be controlled particularly well with the compound of the formula (I) and its salts, in particular its sodium salt, and whose control is less likely to succeed with both conventional herbicides and more recent compounds of a similar molecular structure are, in particular, Agropyron, Alopecurus, Amaranthus, Apera, Avena, Bromus, Capsella, Erysimum, Lolium, Phalaris, Poa, Setaria, Sinapis and Thlaspi.

The compound of the formula (I) and its salts, in particular its sodium salt, can be converted into the customary formulations, such as solutions, emulsions, wettable powders, suspensions, powders, dusts, pastes, soluble powders, granules, suspension/emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ for example organic solvents as auxiliary solvents. Suitable liquid solvents are essentially the following: aromatic hydrocarbons, such as xylene, toluene or alkylnaphthalenes, chlorinated aromatics, such as chlorobenzenes, chlorinated aliphatics, such as chloroethylenes or methylene chloride, aliphatic hydrocarbons, such as cyclohexane or paraffins, petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colourants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the compound of the formula (I) and its salts, as such or in the form of their formulations, can also be used as mixtures with known herbicides, finished formulations or tank mixes being possible.

Possible components for the mixtures are known herbicides, for example amidosulfuron, bentazon, bromoxynil, carfentrazone(-ethyl), cinidon(-ethyl), clodinafop(-propargyl), clopyralid, chlorsulfuron, chlortoluron, cyclosulfamuron, 2,4-D, diclofop(-methyl), difenzoquat, diflufenican, floransulam, flupyrsulfuron(-methyl, -sodium), pyraflufen(-ethyl), ethoxyfen, fenoxaprop (-ethyl), fluoroglycofen(-ethyl), flupropacil, fluroxypyr, iodosulfuron, isoproturon, mecoprop, metosulam, metribuzin, metsulfuron(-methyl), pendimethalin, prosulfocarb, pyridate, sulfosulfuron, thifensulfuron(-methyl), tralkoxydim, triasulfuron, tribenuron(-methyl), trifluralin.

Mixtures with other known active compounds, such as fungicides, insecticides, acaricides, nematicides, bird repellents, plant nutrients and agents which improve soil structure, are also possible.

The compound of the formula (I) and its salts can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The compound of the formula (I) and its salts can be applied either before or after emergence of the plants. They can also be incorporated into the soil before sowing.

The amount of active compound used can vary within a substantial range. It depends essentially on the nature of the desired effect. In general, the amounts used are between 1 g and 1 kg of active compound per hectare of soil surface, preferably between 5 g and 0.5 kg per ha.

The use of the compound of the formula (I) and its salts can be seen from the following examples.

USE EXAMPLES

The compounds listed below are used as comparative substances in the use examples:

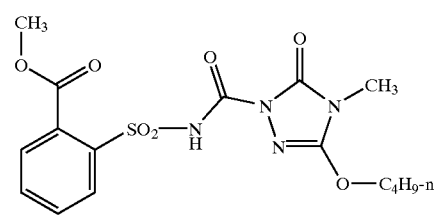

(A)

2-(2-Methoxycarbonyl-phenylsulphonylaminocarbonyl)-4-methyl-5-butoxy-2,4-dihydro-3H-1,2,4-triazol-3-one (known from EP-507 171, U.S. Pat. No. 5,534,486—Example 40)

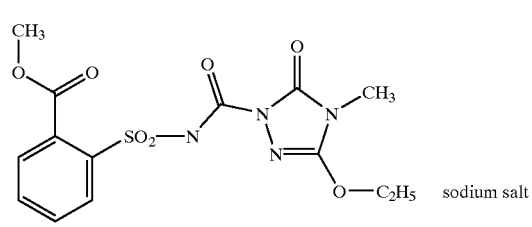

(B)

2-(2-Methoxycarbonyl-phenylsulphonylaminocarbonyl)-4-methyl-5-ethoxy-2,4-dihydro-3H-1,2,4-triazol-3-onesodium salt (known from U.S. Pat. No. 5,534,486—Example 185)

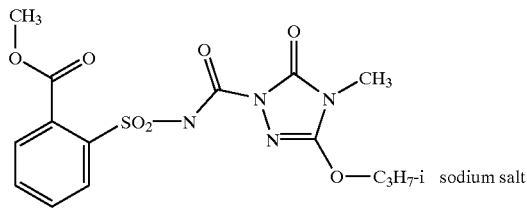

2-(2-Methoxycarbonyl-phenylsulphonylaminocarbonyl)-4-methyl-5-isopropoxy-2,4-dihydro-3H-1,2,4-triazol-3-one-sodium salt (known from U.S. Pat. No. 5,534,486—Example 259)

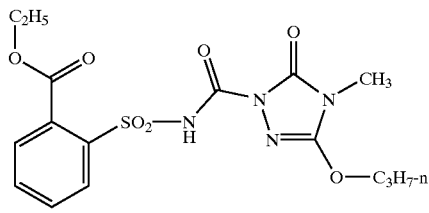

2-(2-Ethoxycarbonyl-phenylsulphonylaminocarbonyl)-4-methyl-5-propoxy-2,4-dihydro-3H-1,2,4-triazol-3-one (in the claim of EP-507 171 and U.S. Pat. No. 5,534,486)

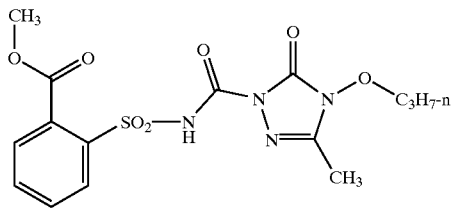

2-(2-Methoxyxcarbonyl-phenylsulphonylaminocarbonyl)-4-propoxy-5-methyl-2,4-dihydro-3H-1,2,4-triazol-3-one (in the claim of EP-341 489 and EP-422 469 and also U.S. Pat. No. 5,057,144)

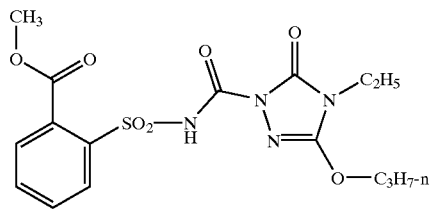

2-(2-Methoxycarbonyl-phenylsulphonylaminocarbonyl)-4-ethyl-5-propoxy-2,4-dihydro-3H-1,2,4-triazol-3-one (in the claim of EP-507 171 and U.S. Pat. No. 5,534,486)

Example A

Post-emergence Test/greenhouse

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit area. The concentration of the spray liquor is chosen so that the particular amounts of active compound desired are applied in 500 l of water/ha. After three weeks, the degree of damage to the plants is assessed in % damage in comparison to the development of the untreated control.

The figures denote:

0%=no effect (like untreated control)

100% total destruction

In this test, for example, the sodium salt of the compound of the formula (I) exhibits, at an application rate of 60 g/ha, very strong activity (efficacy 80% to 100%) against weeds, such as, for example, Agropyron, Alopecurus, Avena, Bromus and Lolium, combined with very good compatibility with crop plants, such as, for example, wheat, whereas the comparative compounds (A), (C), (D), (E) and (F) have considerably weaker herbicidal activity and the comparative compounds (B) and (F) are not entirely compatible with wheat. ["ai."="active ingredient"].

TABLE A

| | Post-emergence test/greenhouse | | | | | | |
|---|---|---|---|---|---|---|---|
| Active compound | Application rate (g ai./ha) | Wheat | Agropyron | Alopecurus | Avena | Bromus | Lolium |
| Comparative compound (A) | 60 | 0 | 0 | 0 | 50 | 0 | 0 |
| Comparative compound (B) | 30 | 60 | 90 | 90 | 90 | 80 | 90 |
| Comparative compound (C) | 60 | 0 | 60 | 70 | 50 | 70 | 70 |
| Comparative compound (D) | 60 | 0 | 70 | — | 20 | 80 | 30 |
| Comparative compound (E) | 250 | 0 | — | 70 | 0 | 50 | 50 |

TABLE A-continued

Post-emergence test/greenhouse

| Active compound | Application rate (g ai./ha) | Wheat | Agropyron | Alopecurus | Avena | Bromus | Lolium |
|---|---|---|---|---|---|---|---|
| Comparative compound (F) | 60 | 20 | 50 | 50 | 40 | 50 | 30 |
| according to the invention: | | | | | | | |
| (I)—Na-salt | 60 | 0 | 100 | 90 | 80 | 95 | 80 |

Example B

Pre-emergence Test/greenhouse

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 500 litres of water per hectare.

After three weeks, the degree of damage to the plants is tested in % damage in comparison to the development of the untreated control.

The figures denote:

0% no effect (like untreated control)

100%=total destruction

In this test, for example, the sodium salt of the compound of the formula (I) exhibits, at application rates of from 15 g/ha to 60 g/ha, very strong activity (efficacy 80% to 100%) against weeds, such as, for example, Agropyron, Alopecurus, Avena, Bromus, Lolium, Poa, Setaria and Sinapis, combined with very good compatibility with crop plants, such as, for example, wheat, whereas the comparative compounds (A), (C), (D), (E) and (F) exhibit considerably weaker herbicidal activity and the comparative compound (B) is not entirely compatible with wheat.

TABLE B1

Pre-emergence test/greenhouse

| Active compound | Application rate (g ai./ha) | Wheat | Alopecurus | Avena | Bromus | Lolium | Setaria |
|---|---|---|---|---|---|---|---|
| Comparative compound (A) | 500 | 0 | 20 | 0 | 30 | 0 | 0 |
| according to the invention: | | | | | | | |
| (I)—Na-salt | 30 | 0 | 95 | 90 | 90 | 80 | 90 |

Table B2

Pre-emergence test/greenhouse

| Active compound | Application rate (g ai./ha) | Wheat | Agropyron | Alopecurus | Avena | Bromus | Lolium | Poa | Setaria |
|---|---|---|---|---|---|---|---|---|---|
| Comparative compound (C) | 30 | 0 | 50 | 70 | 70 | 70 | — | 80 | 70 |
| Comparative compound (D) | 30 | 0 | 60 | 70 | 30 | — | 30 | 70 | 50 |
| according to the invention: | | | | | | | | | |
| (I)—Na-salt | 30 | 0 | 90 | 95 | 90 | 90 | 80 | 95 | 90 |

TABLE B3

Pre-emergence test/greenhouse

| Active compound | Application rate (g ai./ha) | Wheat | Agropyron | Alopecurus | Avena | Bromus | Poa | Amaranthus | Sinapis |
|---|---|---|---|---|---|---|---|---|---|
| Comparative compound (B) | 15 | 40 | 40 | — | 60 | — | 70 | 70 | 70 |
| Comparative compound (F) | 15 | 0 | 0 | 40 | 0 | 20 | 0 | 70 | 70 |
| according to the invention: | | | | | | | | | |
| (I)—Na-salt | 15 | 0 | 90 | 95 | 80 | 90 | 90 | 95 | 90 |

TABLE B4

Pre-emergence test/greenhouse

| Active compound | Application rate (g ai./ha) | Wheat | Alopecurus | Avena | Bromus | Lolium | Setaria |
|---|---|---|---|---|---|---|---|
| Comparative compound (E) | 250 | 0 | 80 | 0 | 0 | 40 | 0 |
| according to the invention: | | | | | | | |
| (I)—Na-salt | 60 | 0 | 95 | 90 | 95 | 80 | 90 |

Example C

Post Emergence Tests/outdoors

Under outdoor conditions, the sodium salt of the compound of the formula (I) was tested in winter wheat in Germany and France against economically important weeds. The small-plot experiments were carried out on cultivated land under agricultural use, with cultivation and climate conditions which can be considered to be representative for the period of the trial. Areas with particularly extensive weed growth were chosen by way of preference.

The active compound was applied by the post-emergence method (spring) across the area by the spray method, with an average droplet size. To produce a useful preparation of active compound, the active compound was formulated as 70 WP or 70 WG (70% w/w water-dispersible powder or granules) and applied with customary amounts of water.

To assess the crop compatibility, from 1 to 8 weeks after the treatment, plant growth inhibitions or ailing of the leaf area were assessed in % damage in comparison to the development of the untreated control. At different intervals after the treatment, the herbicidal activity was assessed as % reduction in comparison to the untreated control, based on the weed development. The figures denote:

0%=no damage of the crops or no herbicidal effect,

100%=total destruction of the crops or the weeds.

The experiments which were carried out show that the sodium salt of the compound of the formula (I) is particularly suitable for controlling the perennial species Agropyron repens, which is difficult to control, and the annual species Alopecurus myosuroides, Apera spica-venti, Capsella bursa-pastoris and Sinapis arvensis in cereals.

["% w/w"=per cent by weight]

TABLE C

Post-emergence tests/outdoors

| Test plants | Number of tests | (I)-Na-salt (42 g of a.i./ha to 45 g of a.i./ha) herbicidal effect (%) |
|---|---|---|
| Agropyron repens | 83 | 89 |
| Alopecurus myosuroides | 204 | 91 |
| Apera spica-venti | 87 | 94 |
| Poa annua | 5 | 67 |
| Capsella bursa-pastoris | 6 | 100 |
| Sinapis arvensis | 4 | 100 |
| Damage to the crop (wheat) | 439 | 2 |

Example D

Post-emergence Tests/outdoors

The sodium salt of the compound of the formula (I) was tested under outdoor conditions in the main cultivation areas of winter wheat in the USA (Pacific Northwest, North Central Area, Central Plains) against economically important weeds. The design, the practice and the evaluation of the experiments corresponded to Example C. The active compound was applied in autumn. Wetting of the plants was improved by addition of commercial surface-active substances (SAS) in the concentrations recommended by the respective manufacturer.

The tests show that the sodium salt of the compound of the formula (I) is particularly suitable for controlling Bromus species, Erysimum cheiranthoides and Thlaspi arvense in cereals.

TABLE D

Post-emergence tests/outdoors

| Test plants | Number of tests | (I)-Na-salt (42 g a.i./ha to 45 g a.i./ha) herbicidal effect (%) |
|---|---|---|
| *Bromus secalinus* | 24 | 95 |
| *Bromus tectorum* | 37 | 90 |
| *Erysimum cheiranthoides* | 10 | 89 |
| *Thlaspi arvense* | 7 | 100 |
| Damage to the crop (wheat) | 78 | 2 |

Example E
Post-emergence Test/outdoors

The sodium salt of the compound of the formula (I) was tested under outdoor conditions in an irrigation wheat growing area of the USA (California) against economically important weeds. The design, the practice and the evaluation of the tests corresponded to Example D.

The tests which were carried out show that the sodium salt of the compound of the formula (I) is particularly suitable for controlling Phalaris species in cereals.

TABLE E

Post-emergence test/outdoors

| Test plants | Number of tests | (I)-Na salt + SAS (42 g a.i./ha to 45 g a.i./ha) herbicidal effect (%) |
|---|---|---|
| *Phalaris minor* | 2 | 93 |
| *Phalaris paradoxa* | 8 | 99 |
| Damage to the crop (wheat) | 7 | 5 |

What is claimed is:

1. A method for the selective control of at least one weed selected from Agropyron, Alopecurus, Avena, Capsella, Erysimum, Lolium, Phalaris, Poa, Setaria, Sinapis, Thlaspi and combinations thereof in a cereal crop comprising applying an effective amount of 2-(2-methoxycarbonyl-phenylsulfonylaminocarbonyl)-4-methyl-5-propoxy-2,4-dihydro-3H-1,2,4-triazol-3-one and/or salts thereof to said crop.

2. The method of claim 1, wherein said crop is wheat.

3. The method of claim 1, wherein said at least one weed is selected from Agropyron, Alopecurus, Avena, Lolium, Poa, Setaria and Sinapis.

4. The method of claim 1, wherein said at least one weed is Alopecurus.

5. The method of claim 1, wherein said at least one weed is Agropyron.

6. The method of claim 1, wherein said 2-(2-methoxycarbonyl-phenylsulfonylaminocarbonyl)-4-methyl-5-propoxy-2,4-dihydro-3H-1,2,4-triazol-3-one and/or salts thereof is applied at an application rate of 15 to 60 g/ha.

7. The method of claim 1 wherein said at least one weed is Alopecurus and said crop is winter wheat.

8. The method of claim 1 wherein said at least one weed is Agropyron and said crop is winter wheat.

9. The method of claim 7, wherein said 2-(2-methoxycarbonyl-phenylsulfonylaminocarbonyl)-4-methyl-5-propoxy-2,4-dihydro-3H-1,2,4-triazol-3-one and/or salts thereof is applied as 70 WP or 70 WG formulation.

\* \* \* \* \*